(12) United States Patent
Nonaka et al.

(10) Patent No.: US 11,832,985 B2
(45) Date of Patent: Dec. 5, 2023

(54) RADIOGRAPHY SYSTEM, RADIOGRAPHY APPARATUS USED IN THE RADIOGRAPHY SYSTEM, AND CONTROL APPARATUS USED IN THE RADIOGRAPHY SYSTEM

(71) Applicant: CANON KABUSHIKI KAISHA, Tokyo (JP)

(72) Inventors: Hideki Nonaka, Kanagawa (JP); Hirokazu Ohguri, Chiba (JP); Taro Hiroike, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 479 days.

(21) Appl. No.: 17/177,844

(22) Filed: Feb. 17, 2021

(65) Prior Publication Data

US 2021/0169435 A1    Jun. 10, 2021

Related U.S. Application Data

(63) Continuation of application No. PCT/JP2019/029944, filed on Jul. 31, 2019.

(30) Foreign Application Priority Data

Aug. 24, 2018 (JP) ................. 2018-157804
Aug. 24, 2018 (JP) ................. 2018-157805
Aug. 24, 2018 (JP) ................. 2018-157806

(51) Int. Cl.
    *A61B 6/00*    (2006.01)
(52) U.S. Cl.
    CPC ............... *A61B 6/54* (2013.01); *A61B 6/566* (2013.01)

(58) Field of Classification Search
    CPC ........ A61B 6/4494; A61B 6/4266; A61B 6/54; A61B 6/547; A61B 6/548; A61B 6/587; A61B 6/032; A61B 6/4417; A61B 6/563; A61B 6/566; H05G 1/56
    See application file for complete search history.

(56) References Cited

FOREIGN PATENT DOCUMENTS

| CN | 105832352 A | * | 8/2016 | ............ A61B 6/00 |
|---|---|---|---|---|
| JP | 2006-320532 A | | 11/2006 | |
| JP | 2008-142314 A | | 6/2008 | |
| JP | 2008-167841 A | | 7/2008 | |
| JP | 2012-100843 A | | 5/2012 | |
| JP | 2017-189325 A | | 10/2017 | |
| JP | 2018-086073 A | | 6/2018 | |
| WO | 2009/031411 A1 | | 3/2009 | |

* cited by examiner

*Primary Examiner* — Don K Wong
(74) *Attorney, Agent, or Firm* — Canon U.S.A., Inc., IP Division

(57) ABSTRACT

A radiography system, comprises: one or more radiography apparatuses configured to detect radiation and capture a radiation image; and a plurality of control apparatuses configured to control the one or more radiography apparatuses, the one or more radiography apparatuses and the plurality of control apparatuses being connected to a communication path. The one or more radiography apparatuses transmit information for identification of the one or more radiography apparatuses to the plurality of control apparatuses in parallel via the communication path, and the plurality of control apparatuses receive the information for identification in parallel.

19 Claims, 4 Drawing Sheets

FIG.2

| ID | COOPERATION STATUS | SIZE | STATUS | TERMINAL BEING IN COOPERATION | CHARGE AMOUNT |
|---|---|---|---|---|---|
| FPD-7 | NOT YET IN COOPERATION | 17 x 14 | GOOD | — | 83% |
| FPD-4 | NOT YET IN COOPERATION | 17 x 14 | GOOD | — | 76% |
| FPD-3 | NOT YET IN COOPERATION | 8 x 10 | GOOD | — | 67% |
| FPD-2 | BEING IN COOPERATION | 17 x 17 | GOOD | Term-2 | 75% |
| FPD-1 | NOT YET IN COOPERATION | 8 x 10 | IN FAILURE | — | — |

FIG.3

| ID | SIZE | STATUS | CHARGE AMOUNT | REMAINING MEMORY CAPACITY |
|---|---|---|---|---|
| FPD-7 | 17 × 14 | PREPARATION FOR IMAGING COMPLETED | 83% | 78% |
| FPD-3 | 8 × 10 | ON STANDBY | 76% | 100% |
| | | | | |
| | | | | |
| | | | | |

RADIOGRAPHY SYSTEM, RADIOGRAPHY APPARATUS USED IN THE RADIOGRAPHY SYSTEM, AND CONTROL APPARATUS USED IN THE RADIOGRAPHY SYSTEM

CROSS-REFERENCE TO RELATED APPLICATIONS

This application is a Continuation of International Patent Application No. PCT/JP2019/029944, filed Jul. 31, 2019, which claims the benefit of Japanese Patent Applications No. 2018-157804 filed Aug. 24, 2018, No. 2018-157805 filed Aug. 24, 2018 and No. 2018-157806 filed Aug. 24, 2018, both of which are hereby incorporated by reference herein in their entirety.

BACKGROUND OF THE INVENTION

Field of the Invention

The present invention relates to a radiography system, a radiography apparatus used in the radiography system, and a control apparatus used in the radiography system which are preferably used for still-image capturing such as general-image capturing for medical diagnosis and moving-image capturing such as fluoroscopic radiography.

Background Art

In recent years, a radiography apparatus using a flat panel detector (hereinafter abbreviated as FPD) formed of a semiconductor material has been used as an imaging apparatus used for medical image diagnosis or non-destructive inspection using X-rays or the like. This FPD has a pixel array in which a plurality of pixels converting radiation to electric signals is arrayed in a two-dimensional matrix, and converts the electric signals from the pixel array to digital data to output a digital radiation image corresponding to one image (frame). Such a radiography apparatus is used, for example, in medical image diagnosis, as a digital imaging apparatus for still-image capturing such as general-image capturing and moving-image capturing such as fluoroscopic radiography.

A radiography system using such a radiography apparatus includes a control apparatus to make inputs of imaging order information such as operation settings of the radiography apparatus, the name of a patient, and an imaging target region, display captured images, and other operations. Patent Literature 1 discusses a radiography system in which a plurality of radiography apparatuses and a plurality of control apparatuses are connected to a communication circuit. In the radiography system discussed in Patent Literature 1, in a case where a management server connected to the communication circuit is in a state of accepting an imaging order from one control apparatus, the management server does not accept an imaging order from another control apparatus. According to Patent Literature 1, this management server prevents overlapping registration of imaging orders from the plurality of control apparatuses to one radiography apparatus, and further prevents a mix-up of radiation images corresponding to patients.

CITATION LIST

Patent Literature

PTL1: Japanese Patent Laid-Open No. 2008-167841

In the technology of Patent Literature 1, however, convergence of information from the plurality of control apparatuses on the management server may have an influence on a system operation such as delay in image display and system operation due to network traffic convergence.

In view of the above-described issue, the present invention is directed to providing a radiography system, in which one or more radiography apparatuses and a plurality of control apparatuses are connected to a communication path, and which is a simple and efficient system without using a management server.

SUMMARY OF THE INVENTION

A radiography system according to the present invention includes one or more radiography apparatuses configured to detect radiation and capture a radiation image, and a plurality of control apparatuses configured to control the one or more radiography apparatuses, the one or more radiography apparatuses and the plurality of control apparatuses being connected to a communication path, wherein the one or more radiography apparatuses transmit information for identification of the one or more radiography apparatuses to the plurality of control apparatuses in parallel via the communication path, and wherein the plurality of control apparatuses receive the information for identification in parallel.

Further features of the present invention will become apparent from the following description of exemplary embodiments with reference to the attached drawings.

BRIEF DESCRIPTION OF THE DRAWINGS

FIG. 2 illustrates a display example of a list of radiography apparatuses serving as cooperation targets.

FIG. 3 illustrates a display example of a list of radiography apparatuses being in cooperation.

DESCRIPTION OF THE EMBODIMENTS

Specific exemplary embodiments of a radiography system according to the present invention will be described below with reference to the accompanying drawings. In the following description and figures, a constituent element common to a plurality of figures is denoted by a common reference sign. Thus, the common constituent element will be described by mutually referring to the plurality of figures, and a description of the constituent element denoted by the common reference sign will be omitted as appropriate. Examples of radiation according to the present invention can include, in addition to α-rays, β-rays, γ-rays, and the like, which are beams composed of particles (including photons) emitted by radiation decay, beams having energy equivalent to or greater than that of the aforementioned beams, such as X-rays, particle rays, and cosmic rays.

First Exemplary Embodiment

Figure 1:
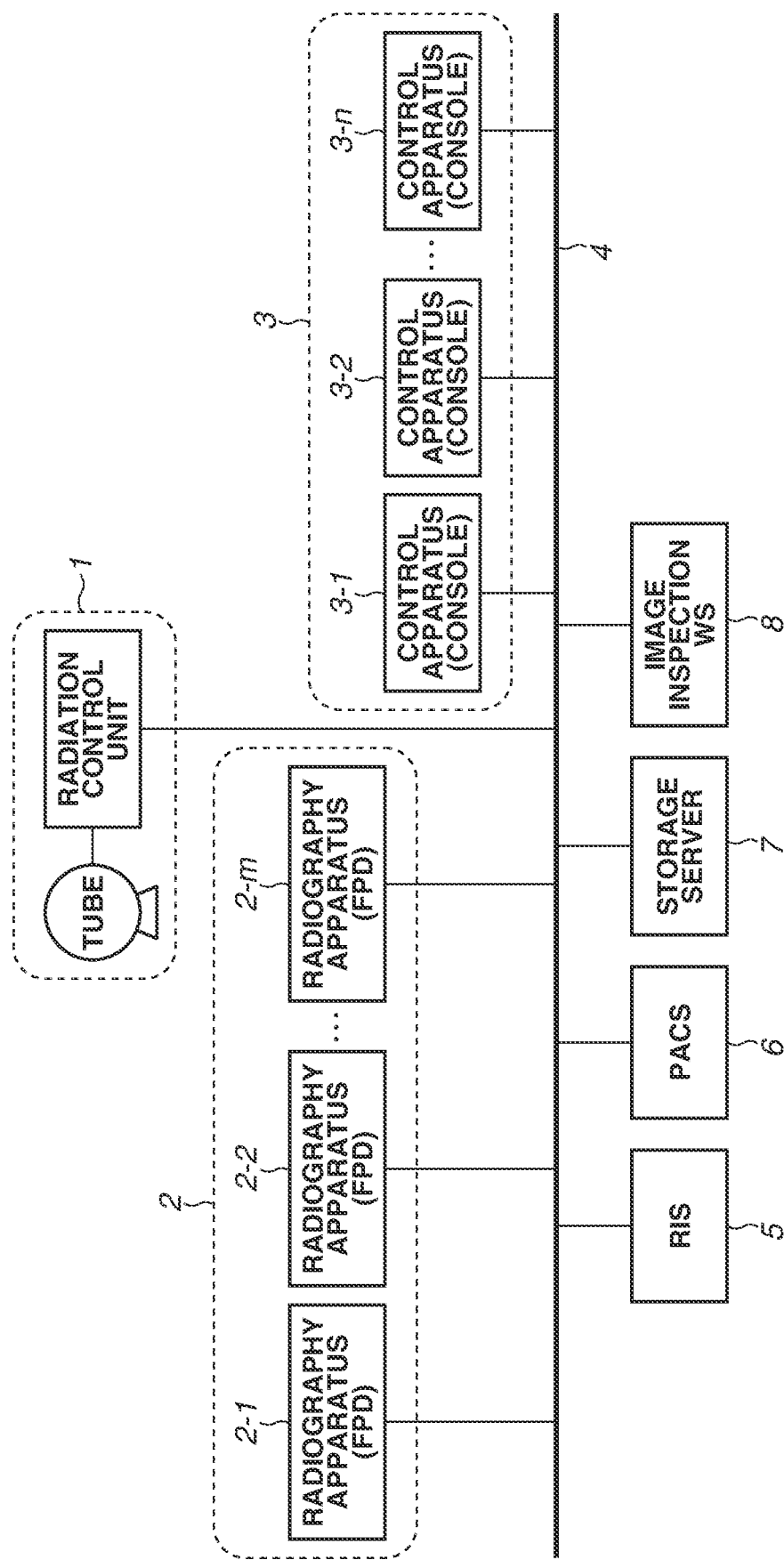
FIG. 1 is a conceptual diagram illustrating a schematic configuration of a radiography system according to a first exemplary embodiment.

FIG. 1 is a configuration diagram illustrating an example of a radiography system according to a first exemplary embodiment of the present invention. The radiography system includes a radiation generation apparatus 1 composed of a radiation control unit and a tube, a radiography apparatus 2 (2-1 to 2-*m*), and a control apparatus 3 (3-1 to 3-*n*). In addition, the radiography system includes a communication path 4, a radiology information system (RIS) 5, and a picture archiving and communication system (PACS) 6. Furthermore, the radiography system includes a storage server 7 and an image inspection workstation 8. The communication path 4 is not limited to an intra-hospital network, and the RIS 5 and the PACS 6 may be connected to an external cloud service or the like. In addition, there are one or more radiation generation apparatuses 1, one or more radiography apparatuses 2, and one or more control apparatuses 3. In particular, the present radiography system is composed of one or more radiography apparatuses and a plurality of control apparatuses 3.

A plurality of control apparatuses 3-1 to 3-*n* can be connected to and cooperate with a plurality of radiography apparatuses 2-1 to 2-*m*. The connection between the control apparatus 3 and the radiography apparatus 2 is established by, for example, wireless local area network (LAN) communication that conforms to Institute of Electrical and Electronics Engineers (IEEE) 802.11. The wireless LAN communication mentioned herein may be communication in a so-called infrastructure mode, in which any one of a wireless LAN communication access point, which is connected to the communication path 4 and not illustrated, the radiography apparatus 2, and the control apparatus 3 performs an access point operation to perform communication. Alternatively, the wireless LAN communication may be communication in an ad-hoc mode, in which the radiography apparatus 2 and the control apparatus 3 directly communicate with each other. In addition, the communication path 4 is not limited to a path for wireless communication, but may be a path for wired communication such as Ethernet. The control apparatus 3 includes a display unit, which can display the status of a connectable radiography apparatus 2 (for example, whether the radiography apparatus 2 is on power saving standby, and whether preparation for imaging has been completed).

Furthermore, an operation from the control apparatus 3 enables control of the radiography apparatus 2 being in cooperation. A radiation image, which is obtained by irradiating the radiography apparatus 2 with radiation, is displayed on the display unit of the control apparatus 3 in cooperation after transferring the radiation image to the control apparatus 3. This allows an operator to check the radiation image after the imaging. In addition, the radiography system associates imaging order information received from the RIS 5 with the radiation image after the imaging, and outputs the radiation image, via the communication path 4, to the storage server 7 that stores an image and the image inspection workstation 8 that performs image processing to generate a final image to be provided for diagnosis.

The control apparatus 3 may be a stationary terminal such as a desktop personal computer (PC) installed in a radiography room, or a built-in terminal installed in a visiting car. Furthermore, the control apparatus 3 may be a mobile terminal such as a personal tablet PC or smartphone of each radiation technologist. Especially in a case of the mobile terminal, which is easy to carry around, utilization of the radiation generation apparatus 1 used for a film-type radiography or a computed radiography (CR) as is for an upgrade to digital radiography (DR) can reduce initial investment. Alternatively, combining the control apparatus 3 with the radiation generation apparatus 1 of an easy-to-carry mobile type is advantageous in availability for emergency medical treatment at a disaster site.

Next, the cooperation between the radiography apparatus 2 and the control apparatus 3 will be described. The plurality of radiography apparatuses 2-1 to 2-*m* and the plurality of control apparatuses 3-1 to 3-*n* are connected to be able to communicate with each other via the communication path 4. The communication path 4 may be either the path for wired communication or the path for wireless communication. One control apparatus 3-*x* can subordinate (cooperate with) the plurality of radiography apparatuses 2 under its control via the communication path 4. That is, the cooperation being established between the radiography apparatus 2 and the control apparatus 3 indicates a status in which the control apparatus 3 can cause the radiography apparatus 2 to perform an imaging operation based on a control instruction from the control apparatus 3 and the radiography apparatus 2 is occupied by the control apparatus 3.

In advance of the operation of the system, the control apparatus 3 and one or more radiography apparatus 2 are brought into cooperation. At this time, information about the above-mentioned one or more radiography apparatuses being connected to the communication path 4 or have been connected to the communication path 4 in the past is displayed on the display unit of the control apparatus 3. In the present exemplary embodiment, a description will be given of a display example of a list that makes the radiography apparatuses 2-1 to 2-*m* identifiable by respective unique names preliminarily allocated thereto, as illustrated FIG. 2. However, the display is not limited to this example. Displaying unique numbers, unique abbreviated names, and unique colors as identification information, or displaying respective icons corresponding to the radiography apparatuses 2-1 to 2-*m* can achieve the same objective.

Selecting the radiography apparatus 2 used for imaging in cooperation with the control apparatus 3 on the list causes a request for cooperation to be transmitted from the control apparatus 3 to the selected radiography apparatus 2. In a case where the radiography apparatus 2 is already "being in cooperation" with another control apparatus at the time of receiving the request for cooperation, the radiography apparatus 2 transmits denial of cooperation to the control apparatus 3 serving as a transmission source of the request for cooperation, and ends the processing. While the description has been given of the case where the control apparatus 3 is capable of making the request for cooperation even in a case where the radiography apparatus 2 is "being in cooperation", it is preferable that selection of cooperation be impossible on the control apparatus 3 in a case where "being in cooperation" is displayed on the list.

In a case where the radiography apparatus 2 is "not yet in cooperation" with another control apparatus at the time of receiving the request for cooperation, the radiography apparatus 2 transmits acceptance of cooperation to the control apparatus 3, which is the transmission source of the request for cooperation, and makes a transition of its cooperation status to "being in cooperation". The description has been given of the case where the cooperation is completed by selecting the radiography apparatus 2 from the list on the control apparatus 3. However, to infallibly reserve the selected radiography apparatus 2, it is preferable that the radiography apparatus 2 serving as a transmission destination of the request for cooperation perform an operation to make the radiography apparatus 2 discriminable from another radiography apparatus 2.

For example, a light emitting diode (LED) can be arranged on the radiography apparatus 2 and caused to blink upon reception of the request for cooperation. The operator recognizes that the radiography apparatus 2 in which the LED is blinking is the radiography apparatus 2 selected as a cooperation target on the control apparatus 3 and reserves the radiography apparatus 2. Thereafter, it is preferable that pressing an operation button of the reserved radiography apparatus 2 by the operator transmit the acceptance of cooperation from the radiography apparatus 2 to the control apparatus 3, which is the transmission source of the request for cooperation, and make a transition of its own cooperation status to "being in cooperation". The operation to the reserved radiography apparatus 2 is not limited to the pressing of the operation button, and can be, for example, an operation to a touch panel, an operation by voice input, or an operation using a specific gesture. The radiography apparatus 2 being in cooperation with any of the control apparatuses 3 may be notified by causing the LED to blink after the cooperation is established.

Another method that may be employed is to arrange a short-range wireless communication unit for communication such as near field communication (NFC) in each of the radiography apparatus 2 and the control apparatus 3 and transmit identification information of the radiography apparatus 2 from the radiography apparatus 2 to the control apparatus 3 when the radiography apparatus 2 and the control apparatus 3 come close to each other. The control apparatus 3 that has received the identification information collates the received identification information with identification information of the radiography apparatus 2 selected from the list, and determines that the cooperation is accepted if the pieces of information match with each other. Next, the control apparatus 3 transmits completion of cooperation to the radiography apparatus 2, and the radiography apparatus 2 that has received the completion of cooperation makes a transition of its own cooperation status to "being in cooperation".

Furthermore, another method is to connect the radiography apparatus 2 and the control apparatus with a cable and transmit identification information of the radiography apparatus 2 from the radiography apparatus 2 to the control apparatus 3 when the radiography apparatus 2 and the control apparatus 3 are connected with each other. The control apparatus 3 that has received the identification information collates the received identification information with identification information of the radiography apparatus 2 selected from the list, and determines that the cooperation is accepted if the pieces of information match with each other. Subsequently, the control apparatus 3 transmits completion of cooperation to the radiography apparatus 2, and the radiography apparatus 2 that has received the completion of cooperation makes a transition of its own cooperation status to "being in cooperation".

In the method of establishing the connection by the short-range wireless communication or the cable, it is preferable that a warning of erroneous selection be issued to the operator when a radiography apparatus 2 that is different from the radiography apparatus 2 selected as the cooperation target on the control apparatus 3 is connected. For example, the LED arranged in the radiography apparatus 2 can be caused to light or blink or a portion of the list displaying the radiography apparatus 2 erroneously connected on the list of the control apparatus 3 is highlighted. Alternatively, erroneous selection being made can be displayed on the screen of the control apparatus 3 or a warning sound can be issued from a sounding generating element arranged in the radiography apparatus 2 or the control apparatus 3.

The description has been given with a workflow of selecting the radiography apparatus 2 as the cooperation target from the list of the control apparatus 3 and then establishing the connection. However, in the method of establishing the connection by the short-range wireless communication or the cable, the operation can also be performed likewise with a workflow of establishing the connection and then selecting the cooperation target.

When the radiography apparatus 2 and the control apparatus 3 are connected with each other by the short-range wireless communication and the cable connection, the radiography apparatus 2 transmits the identification information of the radiography apparatus 2 to the control apparatus 3. The control apparatus 3 highlights the radiography apparatus 2 corresponding to the received identification information on the list. The operator checks highlighted information of the radiography apparatus 2, and presses a cooperation button on the list in a case where the operator recognizes that the radiography apparatus 2 is his/her desired radiography apparatus 2. In response to the cooperation button being pressed, the control apparatus 3 transmits the completion of cooperation to the radiography apparatus 2, and the radiography apparatus 2 that has received the completion of cooperation makes a transition of its own cooperation status to "being in cooperation". Note that each of the request for cooperation, the denial of cooperation, and the completion of cooperation is transmitted/received in the processing described above using a command or a control signal.

Next, a description will be given of cancellation of cooperation between the radiography apparatus 2 and the control apparatus 3. The list of radiography apparatuses 2 being in cooperation is displayed on the control apparatus 3, as illustrated in FIG. 3. The radiography apparatuses 2 presently being in cooperation with the control apparatus 3 are displayed on this list. If a radiography apparatus 2 with which cooperation is to be canceled is selected, the control apparatus 3 transmits a request for canceling cooperation to the radiography apparatus 2. The radiography apparatus 2 that has received the request for canceling cooperation transmits completion of cancellation of cooperation to the control apparatus 3, which is a transmission source of the request for canceling cooperation, and makes a transition of its own cooperation status to "not yet in cooperation". The method of canceling cooperation is not limited thereto, and may be, for example, arranging a selection cancellation button on the operation screen of the control apparatus 3 and operating the selection cancellation button.

Furthermore, a conceivable method is to cancel cooperation by the short-range wireless communication and the cable connection similarly to the case of establishing cooperation. When the radiography apparatus 2 presently being in cooperation with the control apparatus 3 is connected to the control apparatus 3 by the short-range wireless communication and the cable, the radiography apparatus 2 transmits the identification information of the radiography apparatus 2 to the control apparatus 3. The control apparatus 3 highlights the radiography apparatus 2 corresponding to the received identification information on the list. The operator checks the highlighted information of the radiography apparatus 2, and presses a cooperation cancellation button on the list in a case where the operator recognizes that the radiography apparatus 2 is a radiography apparatus 2 of a cooperation cancellation target. In response to the cooperation cancellation button being pressed, the control apparatus 3 transmits the completion of cancellation of cooperation to the radiography apparatus 2, and the radiography apparatus 2 that has received the completion of cancellation of cooperation makes a transition of its own cooperation status to "not yet in cooperation". Note that each of the request for canceling cooperation and the completion of cancellation of cooperation is transmitted/received in the processing described above using a command or a control signal.

In such a radiography system, in order to make an available radiography apparatus 2 selectable, the list is displayed on the control apparatus 3 in a state in which at least part of information (first information) for identification of the plurality of radiography apparatuses 2-1 to 2-m can be viewed. As the first information, operation information such as a status or present operation status of the corresponding radiography apparatus 2 can be displayed together to further facilitate selection. The operator can select the radiography apparatus 2 to be used for imaging based on the first information.

Here, information for identification of each of the radiography apparatuses 2-1 to 2-m, which is transmitted from the radiography apparatus 2 to the control apparatus 3 as the first information, includes at least one of unique information, present status information, position information, cooperation information, or communication status information of each of the radiography apparatuses 2-1 to 2-m.

The unique information of each of the radiography apparatuses 2-1 to 2-m includes, for example, a name, size information indicating a size, communication mode information indicating an executable communication mode, and imaging mode information indicating an executable imaging mode. The name may be a serial number or the like of each of the radiography apparatuses 2-1 to 2-m, or may be a name set by the operator to identify each of the radiography apparatuses 2-1 to 2-m in a facility using the radiography system as indicated by identification (ID) in FIG. 2. The size information is preferably information of a size of the radiography apparatus 2 (in more detail, a size of a pixel region in which imaging can be performed) or the like, to appropriately select the radiography apparatus 2 in accordance with a body type of a patient to be imaged or an imaging procedure. Regarding the communication mode information, there may be a case where a radiography apparatus 2 having a plurality of communication modes such as a wired communication mode using a cable and a wireless communication mode, and a radiography apparatus 2 having only either one of the wired communication mode and the wireless communication mode are present in a mixed manner. Furthermore, there may be a case where communication speed or the like is different. Thus, the communication mode information may be information that enables execution of these modes. The imaging mode information may be information that enables execution of, for example, an imaging mode to perform imaging while communicating with the radiation generation apparatus 1, or an imaging mode in which the radiography apparatus 2 detects by itself the start of irradiation of radiation without communicating with the radiation generation apparatus 1 to perform imaging.

Examples of the present status information indicating the present status of the radiography apparatus 2 include a charging status of a built-in power source mounted in the radiography apparatus 2, a remaining storage capacity, an error status, a failure status, a usage history, and a frequency of usage. The radiography apparatus 2 can not only operate by being supplied with power from the outside, but also operate by being supplied with power from the built-in power source mounted in the radiography apparatus 2. While a secondary battery represented by a lithium-ion battery or a capacitor such as a lithium-ion capacitor is often used as the built-in power source, a power source may be anything that is operable without being supplied with power from the outside, and may be in a removable type or a built-in type. The charging status of the built-in power source may be indicated by a charge amount in percentage, time at which the radiography apparatus 2 is available, or the number of images that can be captured. The radiography apparatus 2 includes a large-capacity nonvolatile memory to hold image data in the radiography apparatus 2 without losing a captured image at time of emergency. In addition, there may be a case where the radiography apparatus 2 has an imaging mode to accumulate captured images in the nonvolatile memory without transmitting an image to the control apparatus 3 every time the imaging is performed, and put together and transmit the captured images to the control apparatus 3 later. This nonvolatile memory is implemented by a NOR flash memory, a NAND flash memory, a Secure Digital (SD) card, or the like. Assume that a remaining storage capacity of this nonvolatile memory is the present status information. The error status and the failure status relate to the internal status of the radiography apparatus 2, and indicate information about whether the radiography apparatus is available for imaging and whether there is a restriction on operations or the like. If the radiography apparatus 2 is unavailable due to a temporary error status or a failure, it is possible to prompt the operator to select another radiography apparatus 2. The information regarding a usage history or a frequency of usage may indicate for what kind of imaging the radiography apparatus 2 has been used, from which control apparatus 3 the radiography apparatus 2 has been used, a usage history or frequency of usage of the radiography apparatus 2 by the control apparatus 3 presently being in cooperation, or the like. Alternatively, the information may indicate, for example, to what extent the radiography apparatus 2 is used as a whole.

The position information of each of the radiography apparatuses 2-1 to 2-m include, for example, positional relationship between the control apparatus 3 and the radiography apparatus 2, and positional relationship between a location where imaging is to be performed and the radiography apparatus 2. The control apparatus 3 and/or a global positioning system (GPS) reception unit arranged in the radiography apparatus 2 or the like may calculate a positional relationship and display the position information. Alternatively, the position information may be position information obtained in a case where the radiography apparatus 2 communicates with the control apparatus 3 whose installation position is fixed or a cradle 9 that houses the radiography apparatus 2, which will be described in detail in a second exemplary embodiment.

Examples of the cooperation information of a cooperation status of each of the radiography apparatuses 2-1 to 2-m include information indicating whether the radiography apparatus 2 is presently in the cooperation status with the control apparatus 3, and if the radiography apparatus 2 is in the cooperation status, information indicating with which control apparatus 3 the radiography apparatus 2 is in cooperation.

The communication status information, which is information about a communication status, indicates a wireless communication status in an environment in which imaging is actually performed, such an imaging location including an imaging room and a location of rounds, a distance between the control apparatus 3 and the radiography apparatus 2, and a positional relationship. An index indicating a signal intensity between apparatuses or the like, such as received signal strength indication (RSSI) and a signal-to-noise ratio, may be used for the communication status. Alternatively, communication speed calculated by preliminarily performing data transfer may be used. Still alternatively, a numeric value may be directly displayed to the operator, or display with scale of several graduations may be performed to enable rough grasping of the status.

Here, information for identification of each of the control apparatuses 3-1 to 3-*n*, which is transmitted from the control apparatus 3 to the radiography apparatus 2 or another control apparatus 3 as the first information, includes the unique information, cooperation information, and communication status information about the control apparatus 3. Examples of the unique information of each control apparatus 3 include a serial number, an Internet Protocol (IP) address, a media access control (MAC) address, and another unique identification information. Each of the cooperation information and the communication status information is similar to that described in the radiography apparatus 2. In addition, it is possible to transmit, as the first information, request information for requesting the information for identification of the radiography apparatus 2 from the control apparatus 3 to each of the radiography apparatuses 2-1 to 2-*m* and date and time information.

The operator identifies each of the radiography apparatuses 2-1 to 2-*m* based on the first information that can be displayed on the list of the control apparatus 3, and brings the radiography apparatus 2 to be used for imaging into cooperation. These pieces of information for identification (the first information) can be transmitted/received between all the radiography apparatuses 2 and all the control apparatuses 3 connected on the identical communication path 4, regardless of whether each of the radiography apparatuses 2-1 to 2-*m* is in the cooperation status with the control apparatus 3, and can be displayed on each control apparatus 3.

These pieces of first information are displayed on the list of the control apparatus 3 in a state in which each of the radiography apparatuses 2-1 to 2-*m* can be viewed. While the first information is displayed in alignment in display order based on predetermined information, it is preferable that the display order be changeable according to the operator's preference. For example, in a case where the operator is about to perform imaging frequently at the rounds, the first information is displayed in descending order of charge amounts with an emphasis on the charge amounts. Furthermore, in a case where the operator wants to use any one of the radiography apparatuses 2-1 to 2-*m* immediately, the first information is displayed in ascending order of distances from the present position of the control apparatus 3. Alternatively, the first information may be displayed in such order as to rank a radiography apparatus 2 suited to a region to be imaged or an imaging procedure specified for the imaging higher in accordance with an imaging order received from the RIS 5.

Subsequently, in a case where one of the plurality of control apparatuses 3 and one radiography apparatus 2 are in the cooperation status, the control apparatus 3 and the radiography apparatus 2 transmit/receive therebetween second information for the radiography apparatus 2 to perform imaging. In such a case, the other control apparatuses 3 and the radiography apparatus 2 do not transmit/receive the second information therebetween. Here, to prevent the transmission/reception, at least one of the radiography apparatus 2 or the control apparatus 3 may not transmit the second information or at least one of the radiography apparatus 2 or the control apparatus 3 may not receive the second information. That is, the second information can be transmitted/received only between the radiography apparatus 2 in cooperation with the control apparatus 3 and the control apparatus 3, and at least one of transmission or reception of the second information to/from the other control apparatuses 3 which are not in cooperation with the radiography apparatus 2 cannot be performed. In addition, it is preferable that the second information be not used as the first information for identification of the plurality of radiography apparatuses 2-1 to 2-*m*. Note that if the radiography apparatus 2 in the cooperation status with the control apparatus 3 makes a transition to the imaging operation, the control apparatus 3 may display the information for performing imaging (the second information).

The information for performing imaging, which is transmitted from the radiography apparatus 2 to the control apparatus 3 as the second information, includes at least one of operation status information indicating an operation status regarding imaging performed by the radiography apparatus 2, event information, image data, or operation log data.

The operation status information is information of the operation status of the radiography apparatus 2, and indicates, for example, whether the radiography apparatus 2 is in a status of being available for imaging, whether the radiography apparatus 2 has detected irradiation of radiation, and whether the radiography apparatus 2 is transferring radiation image data. The radiography apparatus 2 typically has a plurality of power source statuses, and whether the radiography apparatus 2 is available or unavailable for the imaging operation varies in accordance with the statuses. Assume that a status in which power is supplied only to a power-ON trigger detection unit such as a switch arranged in the radiography apparatus 2 is a power-OFF status, and a status in which power is also supplied to digital circuits such as a central processing unit (CPU), a memory, and a logic circuit to cause interfaces and communication of the radiography apparatus 2 to function is a sleep status. In these statuses, a radiation image cannot be captured. A status in which power is also supplied to an analog unit including a radiation detection sensor in accordance with an instruction from an input interface such as the switch arranged in the radiography apparatus 2 or the control apparatus 3, and the radiation detection sensor is available for capturing a radiation image is a ready status. Receiving the operation status information from the radiography apparatus 2 in the cooperation status and displaying the operation status information allows the operator to check whether the radiography apparatus 2 is in a status of being ready to be irradiated with radiation and whether the radiography apparatus 2 operates normally. In addition, communication between the radiography apparatus 2 and the radiation generation apparatus 1, or detection of the start of irradiation of radiation by the radiography apparatus 2 itself causes the control apparatus 3 to display irradiation of radiation, allowing the operator to see that imaging has been performed.

The event information is information regarding occurrence of an error or an abnormal status, or the like. Specific examples of the event information include a failure in the radiography apparatus 2, warning about an operation, occurrence of an error, and occurrence of a communication abnormality between the radiography apparatus 2 and the control apparatus 3. In addition, examples of the event information include detection of irradiation of radiation in a status in which the radiography apparatus 2 is not available for imaging and detection of an impact to the radiography apparatus 2 or dropping of the radiography apparatus 2 by an acceleration sensor or the like. Furthermore, the event information may be information obtained in a case where the charge amount of the built-in power source, the communication status, a temperature of the radiography apparatus 2, or the like exceeds or falls below a predetermined threshold.

Since these pieces of event information are important in performing imaging normally, it is preferable that the occurrence of an event be popped up or highlighted to make the operator easily aware of the occurrence of the event.

The image data is not limited to radiation image data captured by irradiation of radiation, and includes image data for image correction. After being transmitted to the control apparatus 3, the radiation image data is subjected to necessary correction processing and then displayed. To shorten time until the radiation image data is displayed, the radiation image data is divided into several pieces of scaled down image data instead of being maintained in the original size. There may be a case of using a method in which the radiography apparatus 2 sequentially transmits these pieces of scaled down image data to the control apparatus 3 and the control apparatus 3 displays an image with a high resolution while sequentially combining the received pieces of scaled down image data.

The operation log data, which is data of an operation log of the radiography apparatus 2, is obtained by recording time information, the occurrence of an event in the radiography apparatus 2, the transition of the status of the radiography apparatus 2, and the like, and is stored in the nonvolatile memory of the radiography apparatus 2. However, since there is a limitation in storage capacity of the memory, the operation log data is typically transmitted to and stored in the control apparatus 3. The operation log data may be transmitted when a request is made from the control apparatus 3, or may be transmitted from the radiography apparatus 2 at regular intervals. Alternatively, the operation log data may be transmitted by being added to the radiation image data every time a radiation image is captured.

In addition, the information for the radiography apparatus 2 to perform imaging, which is transmitted from the control apparatus 3 to the radiography apparatus 2 as the second information, includes imaging instruction information for instructing the radiography apparatus 2 to perform the imaging operation. The imaging instruction information includes imaging parameter information for setting an imaging parameter of the radiography apparatus 2 in the imaging operation, transition instruction information for instructing a transition of the status of the radiography apparatus 2 to a status of being able to perform the imaging operation, and operation instruction information for instructing the imaging operation of the radiography apparatus 2. The imaging parameter information is information regarding the number of effective pixels, irradiation time (accumulation time), a frame rate, a gain, and sensitivity, which can be set to the radiography apparatus 2, and information regarding an imaging order such as a region to be imaged and an imaging condition. The transition instruction information is, for example, information for making a transition of the status of the radiography apparatus 2 from the sleep status to the ready status. The operation instruction information is, for example, instruction information for acquiring sensor information of a temperature sensor, an acceleration sensor, or the like in the radiography apparatus 2, and information for transmitting a captured image and a log.

Note that even in a case where the control apparatus 3 and the radiography apparatus 2 are in the cooperation status, the control apparatus 3 and the radiography apparatus 2 may transmit/receive the first information therebetween. However, in a case where the control apparatus 3 and the radiography apparatus 2 are in the cooperation status, the transmission/reception of the second information can take precedence over the transmission/reception of the first information.

Here, a description will be given of consistency of information among the plurality of control apparatuses 3-1 to 3-n. An easily conceivable case is that there is the plurality of control apparatuses 3-1 to 3-n in the system. Examples of such a case include a case where there are the control apparatuses 3-1 to 3-n installed in respective ones of a plurality of imaging rooms, and a case where the system is operated such that each of a plurality of operators carries a mobile terminal as any of the control apparatuses 3-1 to 3-n. In this case, it is preferable that list information of the radiography apparatus 2 displayed on each of the plurality of control apparatuses 3-1 to 3-n be always the latest and identical.

Thus, the radiography apparatus 2 can be set so as to transmit the first information to the plurality of control apparatuses 3 at at least one of appropriate timings described below. Examples of timings to transmit the information include a timing when the cooperation status with the control apparatus 3 changes (cooperation is established or canceled), and a timing when the power source status changes (at the time of power-ON or power-OFF). Examples of the timings further include a timing when the operation status makes a transition to the status of being available for imaging or the status of being on standby for imaging, a timing when the radiography apparatus 2 starts or ends transfer of captured image data, a timing when a failure occurs, a timing when time of a preset period elapses, and a timing when the radiography apparatus 2 receives request information from the control apparatus 3. At each of these timings, the radiography apparatus 2 transmits the first information to the control apparatuses 3-1 to 3-n in parallel (at substantially the same time), and the control apparatuses 3-1 to 3-n receive the first information. A display list of each of the control apparatuses 3-1 to 3-n is updated based on the received first information.

At least one of multicasting or broadcasting in a computer network can be used as a unit of transmission at substantially the same time. The multicasting is an operation of transmitting a packet (data) to a plurality of specified network terminals (nodes) in parallel (at substantially the same time). The broadcasting is an operation of transmitting a packet (data) to a large number of unspecified network terminals (nodes) at substantially the same time (in parallel). However, there is no essential difference in effect between the multicasting and the broadcasting, with which one-time transmission of information from the radiography apparatus 2 serving as the transmission source enables simultaneous updating of the information with respect to the plurality of control apparatuses 3-1 to 3-n. As a matter of course, it is possible to achieve the transmission at substantially the same time by performing unicast communication with a single terminal in sequence and in a short period of time.

In addition, at the time of starting and using the control apparatus 3 that has been unused and powered OFF, it is preferable that the cooperation status and operation status of the radiography apparatus 2 be updated to the latest to thereafter establish cooperation. Thus, a status update button is arranged on a user interface of the control apparatus 3, and when the status update button is pressed, the control apparatus 3 transmits request information, which is a request for transmitting the first information, to the plurality of radiography apparatuses 2 at substantially the same time. Alternatively, the control apparatus 3 may be configured, at the time of startup, to infallibly transmit the request information to the plurality of radiography apparatuses 2-1 to 2-m at substantially the same time.

Configuring each of the radiography apparatuses 2-1 to 2-*m* to transmit the first information in response to reception of the request information of the first information updates the display list of the control apparatus 3. While the control apparatus 3 issues the request for transmission of the first information (the request information) to each of the radiography apparatuses 2, the present invention is not limited thereto. Alternatively, the control apparatus 3 may be configured to make a request, to another control apparatus 3 in the system, for transmitting the first information of the radiography apparatus 2 held by the other control apparatus 3, and cause the other control apparatus 3 having received the request to transmit the first information of the radiography apparatus 2. The request for transmission to the other control apparatus 3 at this time may be a request for transmission at substantially the same time with respect to the plurality of control apparatuses 3-1 to 3-*n*. Furthermore, since information regarding the first information of the radiography apparatus 2 in the plurality of control apparatuses 3 remains identical according to the present invention, the transmission may be performed by unicast communication performed with respect to a specified control apparatus 3.

Second Exemplary Embodiment

Figure 4:
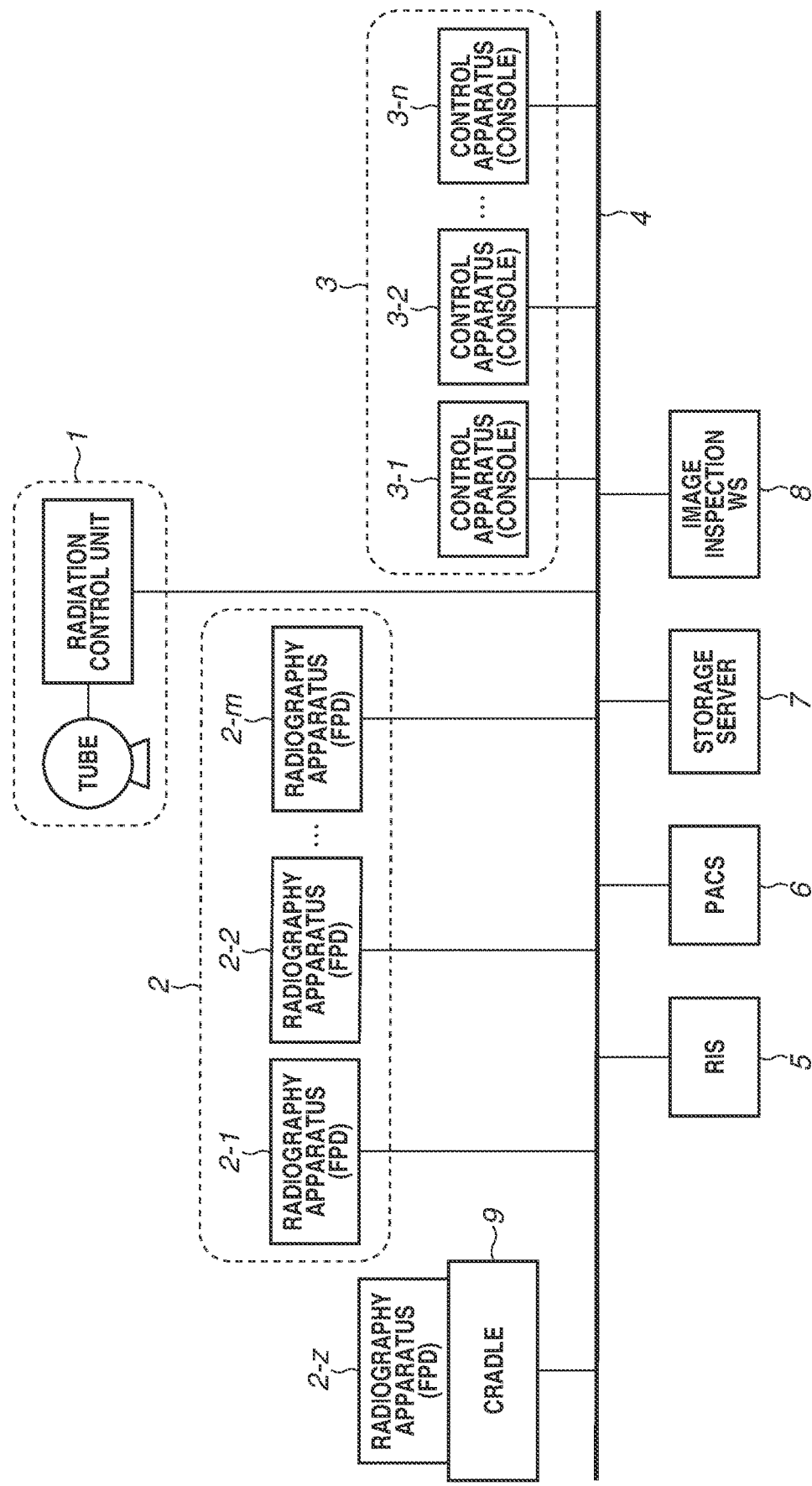
FIG. 4 is a conceptual diagram illustrating a schematic configuration of a radiography system according to a second exemplary embodiment.

Subsequently, the second exemplary embodiment will be described below. FIG. 4 is a block diagram illustrating an example of a radiography system according to the second exemplary embodiment of the present invention. The present exemplary embodiment has the same basic configuration as that of the first exemplary embodiment, and additionally includes a cradle 9 to house the radiography apparatus 2. The cradle mentioned herein is a base to install the radiography apparatus on a table, and is an apparatus capable of performing electronic control such as charging and data transfer. Note that a constituent element similar to that of the first exemplary embodiment is denoted by the same reference sign and the description thereof is omitted.

While the cradle 9 is mainly intended to house and store a radiography apparatus 2-*z* in an unused status, the cradle 9 is preferably provided with a charging function of the built-in power source mounted in the radiography apparatus 2. Furthermore, the cradle 9 is connected to the communication path 4 so as to be able to communicate with another radiography apparatus 2 and the control apparatus 3. Note that connection to the communication path 4 may be either wired connection or wireless connection.

Furthermore, it is preferable that the radiography apparatus 2 be powered OFF while being housed in the cradle 9 in terms of battery consumption and long-term durability of an internal electric component, especially a radiation detector. However, the radiography apparatus 2 in a power-OFF status cannot make a voluntary notification of information or respond to the request for transmission.

Thus, it is preferable that the cradle 9, in substitution for the radiography apparatus 2-*z*, transmit the first information while the radiography apparatus 2-*z* is housed in the cradle 9. During a period since the radiography apparatus 2-*z* is housed in the cradle 9 until the radiography apparatus 2-*z* is powered OFF, the cradle 9 communicates with the radiography apparatus 2-*z* housed therein, reads out the first information, and holds the first information in a storage unit (not illustrated) in the cradle. The communication mentioned herein may be via the communication path 4, or may be performed by arranging another dedicated communication path that directly connects the cradle 9 and the radiography apparatus 2-*z*. In addition, a communication method may be either a wireless communication method or a wired communication method.

A timing of transmission of the first information is similar to that according to the first exemplary embodiment. At this timing, the cradle 9 transmits information that is stored in the storage unit of the cradle 9 and that indicates the radiography apparatus 2-*z* housed in the cradle 9 via the communication path 4.

Furthermore, in a case where the radiography apparatus 2-*z* is removed from the cradle 9, it is preferable that the radiography apparatus 2-*z* be powered ON and the information held in the storage unit in the cradle 9 be deleted to restore the radiography apparatus 2-*z* as an information transmission source from the cradle 9.

As described above, establishment of the cooperation between the radiography apparatus 2 and the control apparatus 3 only involves operations of the radiography apparatus 2 and the control apparatus 3. Accordingly, an associated operation such as a change of an order on a terminal in the upstream of the system, which accompanies replacement of the radiography apparatus to be used, is eliminated and results in an increased operation efficiency. Furthermore, there is no need for a server to perform central control of cooperation between the radiography apparatus 2 and the control apparatus 3. Thus, simplification of the system without the need for the sever is advantageous in terms of cost and management in a small-scale facility that may be operated in a minimum configuration of one radiography apparatus 2 and one control apparatus 3, especially in a facility for a private doctor, a clinic, and the like. Furthermore, in a case where the radiography apparatus 2 and the control apparatus 3 are brought into cooperation with each other, it is possible to check an operation status of each of the radiography apparatuses 2-1 to 2-*m*, reduce downtime of the radiography apparatus 2, and increase operation availability of the system.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiography system, comprising:
one or more radiography apparatuses configured to detect radiation and capture a radiation image; and
a plurality of control apparatuses configured to control the one or more radiography apparatuses, the one or more radiography apparatuses and the plurality of control apparatuses being connected to a communication path,
wherein the one or more radiography apparatuses transmit information for identification of the one or more radiography apparatuses to the plurality of control apparatuses in parallel via the communication path, and
wherein the plurality of control apparatuses receive the information for identification in parallel.

2. The radiography system according to claim 1,
wherein, in a case where, out of the one or more radiography apparatuses and the plurality of control apparatuses that have transmitted/received first information including the information for identification, the one or more radiography apparatuses and one of the plurality of control apparatuses transmit/receive therebetween second information for the one or more radiography apparatuses to perform imaging, at least one of the one or more radiography apparatuses or remaining control apparatuses of the plurality of control apparatuses does not perform at least one of transmission or reception of the second information therebetween.

3. The radiography system according to claim 2,
wherein the information for performing imaging which is transmitted from the one or more radiography apparatuses to the one control apparatus as the second information includes at least one of operation status information indicating an operation status regarding imaging of the one or more radiography apparatuses, event information regarding occurrence of an erroneous status, image data obtained from the one or more radiography apparatuses, or operation log data that is data of an operation log of the one or more radiography apparatuses,
wherein the information for performing imaging transmitted which is from the one control apparatus to the one or more radiography apparatuses as the second information includes imaging instruction information for instructing the one or more radiography apparatuses to perform an imaging operation, and
wherein the imaging instruction information includes at least one of imaging parameter information for setting an imaging parameter of the one or more radiography apparatuses, transition instruction information for instructing a transition of a status of the one or more radiography apparatuses to a status of being able to perform the imaging operation, or operation instruction information for instructing the imaging operation of the one or more radiography apparatuses.

4. The radiography system according to claim 2,
wherein the information for identification transmitted from the one or more radiography apparatuses to the plurality of control apparatuses as the first information includes at least one of unique information of the one or more radiography apparatuses, present information indicating a present status of the one or more radiography apparatuses, position information of the one or more radiography apparatuses, cooperation information about a cooperation status of the one or more radiography apparatuses, or communication status information about a communication status of the one or more radiography apparatuses, and
wherein the information for identification transmitted from the one control apparatus to the one or more radiography apparatuses as the first information includes at least one of unique information of the one control apparatus, cooperation information about a cooperation status of the one control apparatus, or communication status information about a communication status of the one control apparatus.

5. The radiography system according to claim 2,
wherein, even in a case where the one or more radiography apparatuses and the one control apparatus transmit/receive the second information therebetween, the one or more radiography apparatuses and the one control apparatus transmit/receive the first information therebetween.

6. The radiography system according to claim 2,
wherein, in response to reception of request information for making a request for transmission of the first information of the one or more radiography apparatuses from any one of the plurality of control apparatuses, the one or more radiography apparatuses transmit the first information to the plurality of control apparatuses in parallel.

7. The radiography system according to claim 2,
wherein the one or more radiography apparatuses transmit the first information to the plurality of control apparatuses in parallel at at least one of a timing when a cooperation status with the one control apparatus changes, a timing when a power source status of the one or more radiography apparatuses changes, a timing when an operation status of the one or more radiography apparatuses changes, a timing when transfer of image data captured by the one or more radiography apparatuses starts or ends, a timing when a failure of the one or more radiography apparatuses occurs, or a timing when time of a preset period elapses.

8. The radiography system according to claim 6,
wherein the one or more radiography apparatuses transmit the first information to the plurality of control apparatuses in parallel using at least one of multicasting or broadcasting.

9. The radiography system according to claim 7,
wherein the one or more radiography apparatuses comprise a plurality of radiography apparatuses,
wherein each of the control apparatuses includes a display unit configured to display at least part of the first information of the plurality of radiography apparatuses in a viewable state, and
wherein the viewable state is updated in response to reception of the first information transmitted to the plurality of control apparatuses in parallel.

10. The radiography system according to claim 2,
wherein, even in a case where the one or more radiography apparatuses and the one control apparatus transmit/receive the second information therebetween, the one or more radiography apparatuses and the one control apparatus transmit/receive the first information therebetween.

11. The radiography system according to claim 9,
wherein, in a case where at least part of the information for identification of one of the plurality of radiography apparatuses displayed on the display unit of one of the plurality of control apparatuses is selected, the one radiography apparatus and the one control apparatus transmit/receive therebetween the second information for the one radiography apparatus to perform imaging.

12. The radiography system according to claim 11,
wherein, in response to at least part of the information for identification of the one radiography apparatus being selected on the display unit of the one control apparatus, the one control apparatus and the one radiography apparatus transmit/receive the second information therebetween.

13. The radiography system according to claim 11,
wherein each of the one radiography apparatus and the one control apparatus includes a communication unit configured to perform short-range wireless communication,
wherein, in response to the one radiography apparatus and the one control apparatus coming close to each other, at least part of the information for identification is selected, and
wherein, in response to at least part of the information for identification being selected, the one control apparatus and the one radiography apparatus transmit/receive the second information therebetween.

14. The radiography system according to claim 11,
wherein each of the one radiography apparatus and the one control apparatus is configured to be connectable to each other by a cable,
wherein, in response to the one radiography apparatus and the one control apparatus being connected with each other by the cable, at least part of the information for identification is selected, and
wherein, in response to at least part of the information for identification being selected, the one control apparatus and the one radiography apparatus transmit/receive the second information therebetween.

15. The radiography system according to claim 2,
wherein at least one of the plurality of control apparatuses is a mobile terminal.

16. The radiography system according to claim 2, further comprising a cradle configured to house one of the one or more radiography apparatuses to install the one radiography apparatus on a table,
wherein the cradle is connected to the communication path and transmits, in place of the one radiography apparatus, the first information of the one radiography apparatus housed in the cradle.

17. The radiography system according to claim 16,
wherein the cradle includes a storage unit configured to store the first information of the one radiography apparatus.

18. A radiography apparatus used in a radiography system in which one or more radiography apparatuses configured to detect radiation and capture a radiation image and a plurality of control apparatuses configured to control the one or more radiography apparatuses are connected to a communication path,
wherein the radiography apparatus transmits information for identification of the radiography apparatus to the plurality of control apparatuses in parallel via the communication path, the information for identification being received by the plurality of control apparatuses in parallel.

19. A control apparatus used in a radiography system in which one or more radiography apparatuses configured to detect radiation and capture a radiation image and a plurality of control apparatuses configured to control the one or more radiography apparatuses are connected to a communication path,
wherein the control apparatus receives, as one of the plurality of control apparatuses, in parallel with remaining control apparatuses of the plurality of control apparatuses, information for identification of the one or more radiography apparatuses, the information for identification having been transmitted from the one or more radiography apparatuses to the plurality of control apparatuses in parallel via the communication path.

* * * * *